US009867844B2

(12) United States Patent
Han et al.

(10) Patent No.: US 9,867,844 B2
(45) Date of Patent: Jan. 16, 2018

(54) PEPTIDE NUCLEIC ACID OF SUBGROUP J AVIAN LEUKOSIS VIRUS AND USES THEREOF

(71) Applicants: Jianbao Han, Nanjing (CN); Bo Liu, Nanjing (CN)

(72) Inventors: Jianbao Han, Nanjing (CN); Bo Liu, Nanjing (CN)

(73) Assignee: Jianbao Han, Nanjing (CN)

(*) Notice: Subject to any disclaimer, the term of this patent is extended or adjusted under 35 U.S.C. 154(b) by 0 days.

(21) Appl. No.: 15/306,986

(22) PCT Filed: Dec. 10, 2012

(86) PCT No.: PCT/CN2012/001674
§ 371 (c)(1),
(2) Date: Oct. 26, 2016

(87) PCT Pub. No.: WO2013/189003
PCT Pub. Date: Dec. 27, 2013

(65) Prior Publication Data

US 2017/0189442 A1 Jul. 6, 2017

(30) Foreign Application Priority Data

Jun. 20, 2012 (CN) .......................... 2012 1 0205065

(51) Int. Cl.

| | |
|---|---|
| ***C07H 21/04*** | (2006.01) |
| ***A61K 31/7125*** | (2006.01) |
| ***A61K 9/00*** | (2006.01) |
| ***A61K 9/48*** | (2006.01) |

(52) U.S. Cl.
CPC ........ *A61K 31/7125* (2013.01); *A61K 9/0031* (2013.01); *A61K 9/4808* (2013.01)

(58) Field of Classification Search
None
See application file for complete search history.

(56) References Cited

U.S. PATENT DOCUMENTS

2003/0203868 A1 10/2003 Bushman

FOREIGN PATENT DOCUMENTS

CN 102304181 A 1/2012

OTHER PUBLICATIONS

Chen, Mo et al ."Inhibition of avian leukosis virus replication by vector-based RNA interference" Virology, vol. 365, No. 2, Sep. 1, 2007, pp. 464-472.
Meng, Qingwen et al., "Enhanced inhibition of Avian Leukosis virus subgroup J replication by multi-target miRNAs" Virology Journal, vol. 8, No. 556 pp. 1-9, Dec. 2011 (Dec. 31, 2011).
Luessen H L, de leeuw B J, Lang emeyer M, et al. Mucoadhesive polymers in peroral peptide drug delivery. Ö. carbomer and chitosan improve the absorption of the peptide drug buserelin in vivo [ J]. Pharm Res, 1996, 13(11): 1669-1172.
Kotze A F, Luessen H L, de Leeuw B J, et al. Comparison of the effect of different chitosan salts and N—tr—l methyl chitosan chloride on the permeability of intestinal epithelial cells [J]. J Control Release, 1998, 51 (1): 35-46.
T haboo B C, Sunny M C, Jayakrishnan A. Crosslinked chitosan microspheres: preparation and evaluation as a matrix for the controlled release of pharmaceuticals [J]. J Pharm Pharmacol, 1992, 44(4): 283-286.
Portero A, RemunanLo pez C, Criado M T, et al. Reacetylated chitosan microspheres for controlled delivery of antimicrobial agents to the gastric mucosa [J]. J Microencapsul, 2002, 19(6): 797-809.

*Primary Examiner* — Kimberly Chong
(74) *Attorney, Agent, or Firm* — Treasure IP Group, LLC

(57) ABSTRACT

A peptide nucleic acid of subgroup J avian leukosis virus and uses of the same are provided. The sequence of the peptide nucleic acid is one or more selected from the following sequences: sequence 1: 5'AGACUAAGGCAAAAAUCU-GUU-3'; sequence 2: 5'-ACGACUUAUUGAAAAACU-CUC-3'; sequence 3: 5'-UAUAACCGUCUGUAGUUG-GAC-3'; sequence 4: 5'-ACAUAUUUGAUUAUCUCUCCU-3'. The peptide nucleic acid, disclosed in the present invention, can specifically and directly inhibit PRRSV replication, has good antiviral effect and no drug residues, without any toxic side effect and drug resistance.

3 Claims, No Drawings

PEPTIDE NUCLEIC ACID OF SUBGROUP J AVIAN LEUKOSIS VIRUS AND USES THEREOF

BACKGROUND

Technical Field

The present invention relates to a peptide nucleic acid for anti-subgroup J avian AVIAN LEUKOSIS VIRUS and uses thereof.

Related Art

Avian leukosis is a class of infectious diseases caused by avian leukosis virus (ALV) and characterized by malignant proliferation of hematopoietic cells, including lymphoid leukosis (LL), erythroblastic leukosis, myeloblastic leukosis, and myeloid leukosis. Among them, LL causes the greatest hazard to the poultry industry. According to the characteristics of viral envelope, the virus neutralization assay, the host range, and the molecular biological properties of the genome, the virus is classified into 10 subgroups, i.e. subgroups A to J, including all the retroviruses causing neoplastic diseases of poultry except for reticuloendotheliosis virus (REV). The subgroups A, B, C, and D are exogenous viruses, and the subgroups E, F, G, H, and I are endogenous viruses. The subgroups A and B are the exogenous virus subgroups that are mostly commonly found in commercial eggs (Leghorn chickens), the subgroups C and D have an extremely low infection rate and can scarcely be detected, and the subgroup E includes the prevalent low-pathogenic and non-pathogenic endogenous viruses. The subgroup J was initially isolated from commercial generation broilers by Payne and his coworkers in 1988, which is an exogenous leukosis virus that can be widely transmitted horizontally and vertically in the chicken flock when recombined with the endogenous subgroup E. All the breeds of broilers are susceptible to ALV-J; however, the tumor incidence rates of infected chickens differ significantly. Although the layers may be infected with ALV-J, tumor is seldom caused upon natural infection. With the increasingly growth of the poultry industry, the incidence of suspected ALV-J are more wide, causing a high death rate and culling rate of the attacked chicken flock, and bringing a heavy economic loss to the poultry farm.

The disease was epidemic worldwide in 1998, and caused a heavy blow to the poultry industry worldwide. In 1999, the ALV-J virus was initially isolated from and detected in commercial generation broilers by Du Yan et al in China. Since 2000, leukosis subgroup J becomes highly epidemic in the chicken flocks in China, and exhibits an expanded host range. The vertical and horizontal transmission of the virus leads to a clinical and subclinical infection, thus causing a high economic loss.

The economic loss caused by avian leukosis mainly includes the following two aspects: elicitation of tumors, causing the death of chickens; and elicitation of non-neoplastic diseases, causing subclinical infection resulting from immunosuppression, as manifested by emaciation and anemia, tolerant viremia, and immunosuppression of chickens, thereby seriously affecting the poultry production. ALV-J infection may lead to multiple infections of chickens, and several different viruses may be detected simultaneously in individual sick chickens, for example, Reticuloendotheliosis virus (REV), infectious bursal disease viruses (IBDV), and chicken infectious anemia virus (CIAV). During practical production, generally only the impact of tumogenesis on production is noticed, and the subclinical infection is generally ignored. Immunosuppression may include atrophy or agenesia of lymphoid organ, hypergammaglobulinemia, reduced blastocyte formation induced by mitogenic agents and decreased antibody response. Therefore, the loss caused by ALV to the poultry industry is mainly attributed to the earlier non-neoplastic diseases (immunosuppression), and the later death caused by tumors is just a surface phenomenon of immunosuppression from quantitative change to qualitative change.

The clinical symptoms of sick chickens mainly include inappetence, progressive emaciation, abnormal plumage, poor mental state of sick chickens, abdominal distention of some chickens, tangible enlarged liver, pale crest and wattle, crest atrophy of some chickens, visible blood blisters of 1-3 cm on heads, backs, chests, legs, and wings of some chickens that appear brownish purple, touch soft, are elastic to some degree, and have a clear boundary between them and the surrounding skin, unceasing bleeding after rupture of the blood blisters, and contamination of plumage around the blood blisters by large area of blood.

Immunosuppression refers to the fact that the response of an organism to an antigen is low and even deficiency due to the influence arising from various factors (e.g. nutrition, disease, and challenge, etc). The immunosuppression caused by viruses is particularly serious, thus forming immunosuppression. ALV-J may cause myeloid tumors in adult broilers, leading to a high death rate, and cause the reproductivity to decrease (due to the influence on the development of breeding rooster). Due to the death and decreased reproductivity of breeding pullet, the eggs for hatch are reduced, causing a heavy loss to the broiler industry. In addition to the primary infection causing death of chickens, ALV, more importantly, invades immune organs by, for example, causing serious damage to thymus, bursa of Fabricius, and other major immune organs of chickens, resulting in reduced function of the immune organs and decreased resistance to diseases of the organisms, and finally leading to complications and secondary infections. Moreover, it is difficult to eliminate the immunosuppression caused by ALV-J, such that the chicken flocks are unable to respond to or less respond to vaccination, causing failed immunization and thus the outbreak of highly infectious diseases.

Virions have a diameter of 80-100 nm, and are composed of an exterior envelope and an interior nucleocapsid having dense electrons, where the core structure is a regular icosohedron and comprises diploid RNA, nucleocapsid, reverse transcriptase, integrase, and protease. The virus envelope has radial protrusions with a diameter of about 8 nm thereon. The genome of ALV is about 7.2 kb long, and may be directly used as mRNA. The structure of ALV gene is gag-pol-env from 5' to 3' terminus, which encode viral structural proteins, RNA dependent DNA polymerase (reverse transcriptase) and membrane glycoproteins respectively. The gag gene encodes the non-glycosylated structural proteins in the virus, including matrix protein, protease, capsid, and nucleocapsid. In ALV subgroups, these viral proteins are highly conserved and have high homology, that is, the so-called group specific antigen (GSA). The pol gene encodes the reverse transcriptase and integrase of the virus, to complete the integration of viral RNA to proviral DNA and proviral DNA into the cell chromosome, before the cell gene information expression. The env gene encodes the glycosylated proteins on the viral envelope, including the surface glycoprotein subunit (SU) $gp^{85}$ and transmembrane glycoprotein subunit (TM) $gp^{37}$. SU is encoded by the gp85 gene and comprises a virus-receptor determinant determining the specificity of avian leukosis subgroups. TM is response for the transformation of virus into the cells. The long terminal repeats (LTRs) at two sides of the structural gene are correlated with the replication and translation of the viral RNA. The acute transforming ALV also carries a virus-oncogene (v2oncogene). The virus contains 5 structural proteins, that is, Viral group specific antigen capsid protein P27, viral basement membrane protein P19, nucleocapsid protein P12 involved in RNA processing and package, aspartase P15 involved in cleavage of protein precursor, and P10 with unknown functions. The endogenous virus strain RAV-0 has variant P27, namely P27°.

Antisense nucleic acid is a fragment of naturally occurring or artificially synthesized nucleotide sequence that is complementary to a sequence of a target gene (mRNA or DNA), and specifically binds to the viral target gene by base pairing, to form a hybrid molecule, thus playing a role in the regulation of target gene expression at the level of replication, transcription, or translation, or induction of RNase H to recognize and cleave mRNA, such that the function of mRNA is lost.

The antisense nucleic acid includes antisense RNA and antisense DNA, and is characterize by convenient synthesis, simple sequence design, easy modification, high selectivity, and high affinity. As a new anti-viral and anti-tumor agent, the antisense nucleic acid arouses a revolution in the field of pharmacology, that is, new reactions post drug-receptor binding are initiated by a new drug receptor mRNA through the new binding pattern to the receptor (Watson-Crick crossing), including: (1) degradation of the target RNA mediated by RNase H; and (2) inhibition on the DNA replication and transcription and post-transcriptional processing and translation, etc. It is believed that the antisense oligonucleotide (ODNs) therapy is more specific than the conventional drug therapies. Since the late 1970s, the antisense nucleic acid drugs have gone out of the laboratory, and put into practical clinical use in the over three decades of years. The antisense therapy receives great attention especially after the first antisense nucleic acid drug Fomivirsen is approved by FDA.

The mechanism of action of antisense nucleic acid is that based on the principle of base pairing, it is involved in the regulation of relevant gene expression by binding to the target RNA through base pairing. The modes of action may include the following. (1) The anti-sense RNA is bound to the viral mRNA, to from a complementary duplex, thus blocking the binding of ribosome to viral mRNA, and inhibiting the translation of viral mRNA into proteins. (2) The anti-sense DNA can form a triple helix nucleic acid with the target gene, and regulate the transcription of a gene by acting on the transcript, enhancer and primer region controlling the gene transcription. (3) The binding of the antisense nucleic acid to the viral mRNA can prevent the transport of the mRNA to cytoplasm. (4) After the binding of the antisense nucleic acid to the viral mRNA, the mRNA are more easily recognized and degraded by the nuclease, thus greatly reducing the half life of mRNA. The four pathways of action may all be embodied as the inhibition or regulation for viral gene expression, and the regulation is highly specific.

The antisense nucleic acid recognizes the targeting gene based on the principle of base complementation and pairing. Theoretically, for example, the chromosome of animal cells has about several billions of pairs of bases. If the number of the 4 bases (A, G, C, and T) are substantially the same and distributed at random in the whole gene, then the antisense nucleic acid of greater than 17 bases is unlikely to hybridize to a non-target gene according to the principle of statistics. Therefore, the binding of the antisense nucleic acid molecule of greater than 17 bases to the target gene is unique, such that the antisense nucleic acid is highly specific.

Studies show that a copy of gene in the cell can produce 200-300 mRNAs, from which 100,000 biologically active protein molecules are translated. The conventional drugs mainly act on several sites on a domain of the protein molecule having biological functions. Actually, the protein structure is very complex and the spatial structure of active proteins in an organism is versatile. It is difficult to achieve a desirable effect by controlling the dynamics and overall functions of the target molecules via the limited several sites on which the conventional drugs act. Therefore, the limitation of the conventional drugs is obvious. Several dozens to hundreds of protein may be translated from the mRNA, and the target gene is directly regulated by the antisense nucleic acid at the mRNA level, which means that the efficacy of the conventional drugs is increased by several dozens to hundreds of times. It can be seen that the regulation by antisense nucleic acid is quite economic and reasonable.

Toxicological research shows that the antisense nucleic acid has an extremely low toxic in vivo. Although the antisense nucleic acid may remain in vivo for a long or short period of time, it is finally removed by degradation, through which the hazard caused by integration of an exogenous gene into the chromosome of a host in a transgenic therapy is avoided. Compared with the conventional drugs, the antisense nucleic acid drugs have the advantages of high specificity, high efficacy, and low toxic effect, and are useful in the inhibition of tumor growth and viral replication. Currently, numerous drugs become available in American and European markets, and additional 30 antisense nucleic acid drugs are under preclinical study or under phases I, II, and III trial after development.

Due to the large existence of exonucleases in animals, the antisense nucleic acid is quickly degraded and loses the activity if it is not chemically modified. At present, the antisense nucleic acid may be chemically modified through many methods, for example, the common modification of an antisense nucleic acid with phosphorthioate and 2'-methoxy. Moreover, the modification of drugs with phosphorthioate is well studied, and it can effectively resist the degradation by nuclease, and contributes to the activity of the nucleaseRase H. Currently, this modification method is successfully used with the antisense nucleic acid drugs in clinic. However, these are merely modification method for the first generation of antisense nucleic acids. With the development and progression of technologies, new routes and methods of modification will be developed, which allows the research of the second and third generations of antisense nucleic acids to be carried out. Among them, the modification of peptide nucleic acids receives the greatest attention.

Peptide nucleic acids (PNAs) are new analogs of DNA that have neutral amide bonds in the backbone, and can specifically target the groove in DNA. The structural component is N(2-aminoethyl)-glycine, and the bases are attached via methylenecarbonyl to the amino N of the backbone. PNAs are the second generation of antisense nucleic acids.

SUMMARY OF THE INVENTION

An object of the present invention is to provide a peptide nucleic acid.

The peptide nucleic acid provided in the present invention is selected from one or more of the peptide nucleic acids having:

a) a nucleic acid sequence of Sequence 1 as shown in the Sequencing List:

```
                                  (SEQ ID NO: 1)
5'-AGACUAAGGCAAAAAUCUGUU-3';
```

b) a nucleic acid sequence of Sequence 2 as shown in the Sequencing List:

```
                                  (SEQ ID NO: 2)
5'-ACGACUUAUUGAAAAACUCUC-3';
```

c) a nucleic acid sequence of Sequence 3 as shown in the Sequencing List:

```
                                  (SEQ ID NO: 3)
5'-UAUAACCGUCUGUAGUUGGAC-3';
```

and d) a nucleic acid sequence of Sequence 4 as shown in the Sequencing List:

```
                                  (SEQ ID NO: 4)
5'-ACAUAUUUGAUUAUCUCUCCU-3'.
```

The peptide nucleic acid may be a peptide nucleic acid modified with chitosan.

Use of the peptide nucleic acid in the preparation of dugs for anti-avian leukosis virus subgroup J is provided in the present invention.

A peptide nucleic acid preparation having the peptide nucleic acid as an active ingredient is provided in the present invention.

The preparation is in the form of colon specific controlled-release microcapsule preparation, injectable lyophilized preparation or orally taken water-soluble granules.

The peptide nucleic acid preparation of the present invention further comprises a pharmaceutically acceptable carrier or excipient.

Stability analysis of the peptide nucleic acid preparation according to the present invention High temperature: Sterilization for 20 min with flow of high-temperature steam at 105° C., without affecting its biological activity.

Extreme temperature: storage at 50° C. for 6 months without affecting its biological activity.

Room temperature: storage for 24 months without affecting its biological activity.

Low temperature: storage at −20° C. for 48 months without affecting its biological activity.

The peptide nucleic acid of the present invention has no toxic side effect and no resistance, is able to specifically directly inhibit the replication of ALV-J, has a good anti-viral effect, and suffers no food safety problems including drug residue and others.

DETAILED DESCRIPTION

Avian leukosis subgroup J is an infectious disease caused by avian leukosis virus subgroup J (ALV-J) that mainly occurs to chickens, and is characterized by malignant proliferation of hematopoietic cells in chickens. In recent years, the disease has a rapidly rising virus positive rate in the flocks in China and exhibits an expanded host range. The vertical and horizontal transmission of the virus leads to a clinical and subclinical infection, thus causing a high economic loss. By far, there are no effective measures for controlling the disease, and the development of new technologies for preventing and treating ALV-J infection becomes particularly urgent. Furthermore, ALV-J invades the immune system of the chickens, such that the infected flocks are low in immunity, induced immunosuppression, and easily secondarily attacked by other infectious diseases once infected. Up to now, no effective vaccines for preventing the disease are successfully developed. In the present invention, the peptide nucleic acid technology and the antisense nucleic acid technology are combined initially, and used for preventing and treating related diseases caused by ALV-J infection.

For this purpose, the following technical solutions are provided in the present invention.

ALV-J strain: strain NS-X11, available from Nansen Central Laboratory of Veterinary Diagnostic techniques Research.

CEF cells: chick embryo fibroblasts (CEFs) prepared through conventional process.

DF-1 cells: available from Nansen Central Laboratory of Veterinary Diagnostic techniques Research.

In-Vitro Anti-Viral Effect Assay for Peptide Nucleic Acid Anti-ALV-J

The genome of ALV-J was retrieved from the GenBank database, and sequenced by using biological software. By taking the sequence conservation, the percent G+C content, and the base distribution profile into account comprehensively, an antisense nucleic acid was designed by choosing an appropriate region therefrom. The gp85 and P27 genes against the virus finally determined had the following antisense nucleic acid sequences.

```
gp85
gp85-1:
                                  (SEQ ID NO: 5)
5'-AGACUAAGGCAAAAAUCUGUU-3';

gp85-2:
                                  (SEQ ID NO: 6)
5'-UAAAUCGGUGUUGUUAUCGCA-3';
and

gp85-3:
                                  (SEQ ID NO: 7)
5'-ACGACUUAUUGAAAAACUCUC-3';

P27
P27-1:
                                  (SEQ ID NO: 8)
5'-AUAACUCUCAUUAGAUUCGUA-3';

P27-2:
                                  (SEQ ID NO: 9)
5'-UAUAACCGUCUGUAGUUGGAC-3';
and

P27-3:
                                 (SEQ ID NO: 10)
5'-ACAUAUUUGAUUAUCUCUCCU-3'.
```

The peptide nucleic acids having the following peptide nucleic acid sequences were artificially synthesized:

```
gp85
gp85-1:
                                  (SEQ ID NO: 5)
5'-AGACUAAGGCAAAAAUCUGUU-3';

gp85-2:
```

-continued (SEQ ID NO: 6)
5'-UAAAUCGGUGUUGUUAUCGCA-3';
and gp85-3:
(SEQ ID NO: 7)
5'-ACGACUUAUUGAAAAACUCUC-3';

P27
P27-1:
(SEQ ID NO: 8)
5'-AUAACUCUCAUUAGAUUCGUA-3';

P27-2:
(SEQ ID NO: 9)
5'-UAUAACCGUCUGUAGUUGGAC-3';
and

P27-3:
(SEQ ID NO: 10)
5'-ACAUAUUUGAUUAUCUCUCCU-3'.

Chitosan-peptide nucleic acid: peptide nucleic acid modified with chitosan through various methods well known in the art, for example, as specifically described in:

Luessen H L, de leeuw B J, Lang emeyer M, et al. Mucoadhesive polymers in peroral peptide drug delivery. Ö. carbomer and chitosan improve the absorption of the peptide drug buserelin in vivo [J]. Pharm Res, 1996, 13(11): 1668-1172.

Kotze A F, Luessen H L, de Leeuw B J, et al. Comparison of the effect of different chitosan salts and N-tr-I methyl chitosan chloride on the permeability of intestinal epithelial cells [J]. J Control Release, 1998, 51 (1): 35-46.

T hanoo B C, Sunny M C, Jayakrishnan A. Crosslinked chitosan microspheres: preparation and evaluation as a matrix for the controlled release of pharmaceuticals [J]. J Pharm Pharmacol, 1992, 44(4): 283-286.

Portero A, RemunanLo pez C, Criado M T, et al. Reacetylated chitosan microspheres for controlled delivery of anti-microbial agents to the gastric mucosa [J]. J Microencapsul, 2002, 19(6): 797-809.

The inhibition of the peptide nucleic acid on the target viral gene was detected by using quantitative RT-PCR specific for ALV-J, and the anti-viral titer was determined by viral titer assay.

Day 1:

Plating: The DF-1 cells, prepared at an earlier stage of digestion, were collected by centrifugation, counted, adjusted to a cell density of 3-6×$10^5$ cells/ml with a complete medium (DMEM+5% fetal bovine serum+penicillin), plated in a 24-well plate, and incubated for 18-24 hrs at 37° C. in a carbon dioxide incubator.

Day 2:

The cell density was microscopically observed. When the cells were grown over to 70-80% of the area of the plate and grown well, the medium was aspirated off, 300 μl of the agents (that is, the peptide nucleic acids) to be screened were added per well, each agent having 10 wells. After incubation for 1 hr, 100 μl of ALV-J (with the infection rate being 0.01) was added. After 2 hr-adsorption, the unadsorbed viruses were washed off with a nutrient solution, then 4% FBS in DMEM medium was added, and contiuously cultured at 37° C. in 5% $CO_2$. The cytopathic effect was peridically observed after infection. 72 hrs after infection, the infected cells were repeatedly frozen and thrawed, to release the viruses, and this was used as a sample for virus detection. During experiment, a normal cell control group with no virus and peptide nucleic acid, a positive control group with viruses and no peptide nucleic acid, and a negative control group with peptide nucleic acid and no viruses were also set.

Days 3-5:

The protection effect of the agent for cells were observed, and the result was evaluated.

Quantitative Detection by Real-Time PCR

The supernatant of each treatment group was collected, and the viral RNA was extracted by using a total viral RNA extraction kit. The obtained viral RNA was reversely transcripted into cDNA, and then the viral content of the treatment group with ALV-J was detected respectively by using specific Primers. From the results after quantitative amplification, the virus titer and the inhibitory effect of each treatment group in fold differences between the PNA group and the blank control group were calculated by using statistical software.

In the present invention, ALV-J was quantitatively detected by real-time PCR using primers provided by Huang et al.

Primers specific for detection of ALV-J
Primer 1:
(SEQ ID NO: 11)
5'-TCAGGACCAAGGGCTTAC-3';
and Primer 2:
(SEQ ID NO: 12)
5'-CTGCCGCTATAACCGTCTG-3'.

β-actin as internal reference
Actin-F:
(SEQ ID NO: 13)
5'-TCCCTGTATGCCTCTGGTC-3';
and Actin-R:
(SEQ ID NO: 14)
5'-TCTCTCTCGGCTGTGGTGG-3'.

Reaction System (25 μl)

| Reagent | Amount (μl) |
|---|---|
| 2 × One-Step SYBR RT-PCR Buffer | 12.5 |
| Ex TaqTM HS | 0.5 |
| PrimeScriptTM RT Enzyme Mix II | 0.5 |
| Forward PCR primer | 0.5 |
| Reverse PCR primer | 0.5 |
| Total RNA | 2 |
| RNase free $dH_2O$ | 8.5 |
| In total | 25 |

Reaction condition
Reverse transcription
5 min at 42° C.
10 sec at 95° C.
PCR amplification
Cycle: 40
5 sec at 95° C.
30 sec at 60° C.

After the reaction was completed, the amplification and melting curves from the Real Time One Step RT-PCR were confirmed, to ensure the specificity and reliability of the results.

In-Vitro Anti-Viral Result of Peptide Nucleic Acid Anti-ALV-J

The detection results from quantitative PCR show that except for gp85-2 having an unobvious effect, the inhibition rates by gp85-1 and gp85-3 are respectively 78% and 83%

(Table 1); and except for P27-1 having an unobvious effect, the inhibition rates by P27-2 and P27-3 are respectively 73% and 77% (Table 1).

TABLE 1

In-vitro anti-PRRSV effect of peptide nucleic acids for MARC-145 cells

| Group | | Virus inhibition rate 72 h |
|---|---|---|
| Infection and treatment group | gp85-1 group | 78% |
| | gp85-2 group | 23% |
| | gp85-3 group | 83% |
| | P27-1 group | 17% |
| | P27-2 group | 73% |
| | P27-3 group | 77% |
| Virus control group | | — |
| Negative control group | | — |
| Blank control group | | — |

Peptide nucleic acids gp85-⅓ and P27-⅔ are preferred.

Treatment with Drugs in Combination

According to the screening result above, the screened drugs having potent anti-viral effect are used in combination on the basis of the experiments above, to compare the difference of the anti-viral effects between the combined agents and a single agent. After the DF-1 cells were infected with ALV-J strain NS-X11, gene drug combinations of gp85 or P27 were added respectively, and a positive, negative, and blank control group were also set. The detection was performed by Real-time PCR, and the virus inhibition rate in each treatment group was statistically analyzed, as described above. The results are shown in Table 2.

TABLE 2

In-vitro anti-ALV-J effect of various concentrations of peptide nucleic acids for DF-1 cells

| Group | | Virus inhibition rate 72 h |
|---|---|---|
| Infection and treatment group | gp85-1/3 group | 79% |
| | P27-2/3 group | 81% |
| | gp85-1/3 + P27-2/3 group | 88% |
| Virus control group | | — |
| Negative control group | | — |
| Blank control group | | — |

Cell Toxicity Test

1) The object to be detected was DF-1 cells. 100 μl containing 5000 cells was added per well to a 96-well plate. Peptide nucleic acids gp85-1, gp85-3, P27-2 and P27-3 at concentrations of 0.02, 0.1, 0.5, 1, 5, and 10 μm were used, each concentration were performed in triplicate. An untreated cell control and a cell free medium control were additionally set.

2) After treatment, 10 μl of MTT Stock was added per well per 100 μl of medium, and continuously incubated for 4 hrs in an incubator at 37° C. Alternatively, the medium was replaced with 100 μl of fresh serum-free medium, and then MTT Stock was added.

3) The medium was aspirated off, 100 μl of MTT lysing agent was added per well, and the volume of the liquid in each well was kept consistent.

4) The absorbance (OD) was measured at 570 nm, and comparison and calculation were performed. Note: considering the accuracy, the absorbance (OD) of unreduced MTT was measured at 699 nm, which is then subtracted from $OD_{570}$.

5) Determination of result: cell proliferation or toxicity=100%×($OD_{experiment}$−$OD_{background}$)/($OD_{control}$−$OD_{background}$).

$OD_{experiment}$ is the OD value of treated cells, $OD_{control}$ is the OD value of untreated cells in the control tube, $OD_{background}$ is the OD value of the cell free medium control. The change in cell proliferation or toxicity after treatment is expressed as percentage of the untreated control.

The detection result shows that the peptide nucleic acids gp85-1, gp85-3, P27-2 and P27-3 against ALV-J are non-toxic.

Infection and Breeding of Laboratory Animals 200 of healthy AA commercial generation broilers aged 1 day (provided by animal farm of Nansen Central Laboratory of Veterinary Diagnostic techniques Research and detected to be ALV-J negative) were assigned to 5 groups at random. The ALV-J infected group (test group) had 40 animals, and the animals were infected by hypodermically inoculating, at the neck, an ALV-J cell culture at a dosage of 0.2 mL/animal at the age of 1 day. The blank control group (control group) had 40 animals, and the animals received no treatment. The animals in the group dosed with a mixture of gp85-⅓+P27-⅔ peptide nucleic acids at equal weight ratio (25 ppm, 50 ppm, 100 ppm) were administered via drinking water, and bred with strict isolation. The feedstuff and water for each group were prepared separately without crossing.

After ALV-J infection, blood was sampled from chickens at various times, and the serum was isolated, and detected for the virus positive rate by ELISA. The result is shown in Table 3.

TABLE 3

Determination result of ALV-J positive events in serum from animals in each group

| Time (day) | | 1 | 3 | 5 | 7 | 9 |
|---|---|---|---|---|---|---|
| Infection and treatment group | 25 (ppm) | + | + | + | − | − |
| | 50 (ppm) | + | + | − | − | − |
| | 100 (ppm) | + | − | − | − | − |
| Infection group without treatment | | + | + | + | + | + |
| Blank control group | | − | − | − | − | − |

Finally, the preferred dosage is 50-100 ppm.

Growth of Broilers after Viral Infection

No death occurs in the control group.

Death occurs in the mixed infection group in 1 week after viral infection.

The death rates caused by ALV-J infection at week 3 after viral infection are different in each treatment group. The result is shown in Table 4.

The clinical manifestations, weight gain, immune organ index, and death rate of the broilers were also detected. (1) Clinical manifestations, weight gain, and immune organ index. The disease development and growth of the chicken flocks were observed daily, and the weight of the animals in each group was weighed at days 7, 14, 21, 28, 35, and 49. 5 animals in the virus infected groups and 3 animals in the control group were sacrificed at random weekly, and the thymus, spleen, and bursa of Fabricius was removed and weighed respectively at days 7, 21, 35, and 49. The immune organ index was calculated according to the formula: immune organ index=weight of immune organs (g)/live chicken weight (kg). (2) Statistical calculation of death rate. The number of chickens naturally died was recorded every day, and the death rate in each group was statistically calculated. Moreover, necropsy of the animals was carried out, to observe the lesions. (3) Statistical analysis of data.

TABLE 4

Influence on weight of broilers at various age of days after ALV-J infection

| Age in day | ALV-J infected group 25 | 50 | 100 | Blank control group |
|---|---|---|---|---|
| 7 | 149 ± 32 | 136 ± 32 | 129 ± 32 | 128 ± 23 |
| 14 | 362 ± 49 | 375 ± 51 | 392 ± 38 | 350 ± 38 |
| 21 | 502 ± 55 | 542 ± 54 | 532 ± 55 | 560 ± 54 |
| 28 | 650 ± 75 | 700 ± 85 | 670 ± 65 | 708 ± 65 |
| 35 | 998 ± 89 | 1088 ± 89 | 996 ± 92 | 1260 ± 59 |
| 49 | 1590 ± 120 | 1688 ± 140 | 1650 ± 130 | 2020 ± 45 |

As for the influence on the immune organ index of chickens after viral infection, the central immune organ (bursa of Fabricius and thymus) indexes of the ALV-J infected group after 5 weeks are significantly and extremely significantly lower than those of the control group, as shown in 5.

TABLE 5

Influence on immune organ indexes of broilers after ALV-J infection

| Age in day | | Group with ALV-J infection group + drug treatment | Blank control group |
|---|---|---|---|
| | Thymus | 2.9 ± 0.32 | 2.86 ± 0.35 |
| 7 | Bursa of Fabricius | 1.29 ± 0.22 | 1.65 ± 0.4 |
| | Spleen | 0.9 ± 19 | 1.15 ± 0.2 |
| | Thymus | 3.5 ± 0.36 | 3.66 ± 0.34 |
| 21 | Bursa of Fabricius | 2.33 ± 0.23 | 2.65 ± 0.42 |
| | Spleen | 1.1 ± 0.17 | 2.55 ± 0.29 |
| | Thymus | 2.9 ± 0.33 | 4.86 ± 0.55 |
| 35 | Bursa of Fabricius | 1.33 ± 0.31 | 1.65 ± 0.4 |
| | Spleen | 1.5 ± 0.27 | 1.23 ± 0.32 |
| | Thymus | 3.1 ± 0.46 | 5.26 ± 0.17 |
| 49 | Bursa of Fabricius | 0.93 ± 0.18 | 1.35 ± 0.4 |
| | Spleen | 1.21 ± 0.23 | 1.25 ± 0.3 |

What is claimed is:

1. An anti-avian leukosis virus subgroup J (ALV-J) drug comprising four peptide nucleic acids as active components, wherein the sequences of the four peptide nucleic acids are SEQ ID Nos:1-4, respectively a) a nucleic acid sequence of Sequence 1 as shown in the Sequencing List of:

(SEQ ID NO: 1)
5'-AGACUAAGGCAAAAAUCUGUU-3';

b) a nucleic acid sequence of Sequence 2 as shown in the Sequencing List of:

(SEQ ID NO: 2)
5'-ACGACUUAUUGAAAAACUCUC-3';

c) a nucleic acid sequence of Sequence 3 as shown in the Sequencing List of:

(SEQ ID NO: 3)
5'-UAUAACCGUCUGUAGUUGGAC-3';

and d) a nucleic acid sequence of Sequence 4 as shown in the Sequencing List of:

(SEQ ID NO: 4)
5'-ACAUAUUUGAUUAUCUCUCCU-3'.

2. The peptide nucleic acid drug according to claim 1, wherein the peptide nucleic acid formulation is a colon specific controlled-release microcapsule formulation, injectable lyophilized formulation or water-soluble granules for oral use.

3. The peptide nucleic acid according to claim 1, wherein the peptide nucleic acid formulation, further comprises a pharmaceutically acceptable carrier or excipient.

* * * * *

SEQUENCE LISTING

```
<160> NUMBER OF SEQ ID NOS: 14

<210> SEQ ID NO 1
<211> LENGTH: 21
<212> TYPE: RNA
<213> ORGANISM: Artificial Sequence
<220> FEATURE:
<223> OTHER INFORMATION: synthetic

<400> SEQUENCE: 1

agacuaaggc aaaaaucugu u                                    21


<210> SEQ ID NO 2
<211> LENGTH: 21
<212> TYPE: RNA
<213> ORGANISM: Artificial Sequence
<220> FEATURE:
<223> OTHER INFORMATION: synthetic

<400> SEQUENCE: 2

acgacuuauu gaaaaacucu c                                    21


<210> SEQ ID NO 3
<211> LENGTH: 21
<212> TYPE: RNA
<213> ORGANISM: Artificial Sequence
<220> FEATURE:
<223> OTHER INFORMATION: synthetic

<400> SEQUENCE: 3

uauaaccguc uguaguugga c                                    21


<210> SEQ ID NO 4
<211> LENGTH: 21
<212> TYPE: RNA
<213> ORGANISM: Artificial Sequence
<220> FEATURE:
<223> OTHER INFORMATION: synthetic

<400> SEQUENCE: 4

acauauuuga uuaucucucc u                                    21
```

-continued

<210> SEQ ID NO 5
<211> LENGTH: 21
<212> TYPE: RNA
<213> ORGANISM: Artificial Sequence
<220> FEATURE:
<223> OTHER INFORMATION: synthetic

<400> SEQUENCE: 5
agacuaaggc aaaaaucugu u 21

<210> SEQ ID NO 6
<211> LENGTH: 21
<212> TYPE: RNA
<213> ORGANISM: Artificial Sequence
<220> FEATURE:
<223> OTHER INFORMATION: synthetized

<400> SEQUENCE: 6
uaaaucggug uuguuaucgc a 21

<210> SEQ ID NO 7
<211> LENGTH: 21
<212> TYPE: RNA
<213> ORGANISM: Artificial Sequence
<220> FEATURE:
<223> OTHER INFORMATION: synthetized

<400> SEQUENCE: 7
acgacuuauu gaaaaacucu c 21

<210> SEQ ID NO 8
<211> LENGTH: 21
<212> TYPE: RNA
<213> ORGANISM: Artificial Sequence
<220> FEATURE:
<223> OTHER INFORMATION: synthesized

<400> SEQUENCE: 8
auaacucuca uuagauucgu a 21

<210> SEQ ID NO 9
<211> LENGTH: 21
<212> TYPE: RNA
<213> ORGANISM: Artificial Sequence
<220> FEATURE:
<223> OTHER INFORMATION: synthesized

<400> SEQUENCE: 9
uauaaccguc uguaguugga c 21

<210> SEQ ID NO 10
<211> LENGTH: 21
<212> TYPE: RNA
<213> ORGANISM: Artificial Sequence
<220> FEATURE:
<223> OTHER INFORMATION: synthesized

<400> SEQUENCE: 10
acauauuuga uuaucucucc u 21

<210> SEQ ID NO 11
<211> LENGTH: 18
<212> TYPE: DNA
<213> ORGANISM: Artificial Sequence
<220> FEATURE:
<223> OTHER INFORMATION: primer -continued

```
<400> SEQUENCE: 11

tcaggaccaa gggcttac                                                  18


<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12

ctgccgctat aaccgtctg                                                 19


<210> SEQ ID NO 13
<211> LENGTH: 19
<212> TYPE: DNA
<213> ORGANISM: Artificial Sequence
<220> FEATURE:
<223> OTHER INFORMATION: probe or internal reference

<400> SEQUENCE: 13

tccctgtatg cctctggtc                                                 19


<210> SEQ ID NO 14
<211> LENGTH: 19
<212> TYPE: DNA
<213> ORGANISM: Artificial Sequence
<220> FEATURE:
<223> OTHER INFORMATION: probe or internal reference

<400> SEQUENCE: 14

tctctctcgg ctgtggtgg                                                 19
```